US007740897B2

(12) United States Patent
Marx et al.

(10) Patent No.: US 7,740,897 B2
(45) Date of Patent: Jun. 22, 2010

(54) PROCESS FOR PRODUCING RIGID RETICULATED ARTICLES

(75) Inventors: Jeffrey G. Marx, Downingtown, PA (US); Bradley R. Heckendorf, Menomonie, WI (US); James R. Johnson, Boca Raton, FL (US); John Jeffrey Venarsky, Godfrey, IL (US)

(73) Assignee: Wright Medical Technology, Inc., Arlington, TN (US)

( * ) Notice: Subject to any disclaimer, the term of this patent is extended or adjusted under 35 U.S.C. 154(b) by 978 days.

(21) Appl. No.: 11/245,369

(22) Filed: Oct. 6, 2005

(65) Prior Publication Data

US 2006/0093729 A1 May 4, 2006

Related U.S. Application Data

(60) Division of application No. 09/440,144, filed on Nov. 15, 1999, now Pat. No. 6,977,095, which is a continuation-in-part of application No. 08/942,557, filed on Oct. 1, 1997, now Pat. No. 6,136,029.

(51) Int. Cl.
*A61F 2/28* (2006.01)
*A61L 27/32* (2006.01)
*B05D 3/02* (2006.01)

(52) U.S. Cl. ............... 427/2.26; 427/2.27; 427/379; 427/380; 427/381; 623/16.11; 623/23.56; 623/23.61

(58) Field of Classification Search ........... 427/2.1, 427/2.26, 2.27, 379–381; 623/16.11, 23.61, 623/23.56

See application file for complete search history.

(56) References Cited

U.S. PATENT DOCUMENTS

| 3,090,094 A | 5/1963 | Schwartzwalder et al. |
| 3,616,841 A | 11/1971 | Walz |
| 3,662,405 A | 5/1972 | Bortz et al. |
| 3,790,365 A | 2/1974 | Niebylski et al. |

(Continued)

FOREIGN PATENT DOCUMENTS

| DE | 196 10 715 C1 | 6/1997 |
| EP | 0 157 974 A1 | 10/1985 |
| EP | 263489 A1 * | 4/1988 |
| EP | 0 299 342 A1 | 1/1989 |
| EP | 0 335 359 A2 | 4/1989 |

(Continued)

OTHER PUBLICATIONS

Aksaci et al., "Porous Fluorospatite/Spinal Osteoceramic for Bone Bridges", *Bioceramics: Materials and Applications*, 1995, pp. 283-300, Amer. Cer. Soc.

(Continued)

*Primary Examiner*—Timothy H Meeks
*Assistant Examiner*—Cachet I Sellman
(74) *Attorney, Agent, or Firm*—Womble Carlyle Sandridge & Rice, PLLC (57) ABSTRACT

A method for forming a ceramic article useful as a bone substitute and having an outer surface defining a shape having a bulk volume and having open, interconnecting openings extending throughout the volume and opening through the surface, includes, providing an organic open-pore structure, coating surface of pores of the structure with a ceramic slip, pyrolyzing the organic structure to leave a ceramic structure having struts defining a plurality of interconnecting interstices, and providing within the interstices a porous osteoconductive composition exposed to the interconnecting openings. In a preferred embodiment, the ceramic slip includes a strong, supportive ceramic material and a separate osteoconductive material.

20 Claims, 4 Drawing Sheets

U.S. PATENT DOCUMENTS

| | | | |
|---|---|---|---|
| 3,816,952 A | 6/1974 | Niebyski et al. | |
| 3,829,326 A | 8/1974 | Soejima et al. | |
| 3,899,556 A | 8/1975 | Heide et al. | |
| 3,905,047 A | 9/1975 | Long | |
| 4,000,525 A | 1/1977 | Klawitter et al. | |
| 4,070,514 A * | 1/1978 | Eatherly et al. | 428/64.1 |
| 4,073,999 A * | 2/1978 | Bryan et al. | 428/312.8 |
| 4,076,888 A | 2/1978 | Perugini et al. | |
| 4,131,597 A * | 12/1978 | Bluethgen et al. | 523/114 |
| 4,158,684 A | 6/1979 | Klawitter et al. | |
| 4,168,326 A | 9/1979 | Broemer et al. | |
| 4,222,128 A | 9/1980 | Tomonaga et al. | |
| 4,237,559 A | 12/1980 | Borom | |
| 4,264,640 A * | 4/1981 | Infante | 427/2.26 |
| 4,343,704 A | 8/1982 | Brockmeyer | |
| 4,365,356 A | 12/1982 | Broemer et al. | |
| 4,371,484 A | 2/1983 | Inukai et al. | |
| 4,517,069 A | 5/1985 | Harney et al. | |
| 4,596,574 A | 6/1986 | Urist | |
| 4,599,085 A | 7/1986 | Riess et al. | |
| 4,626,392 A | 12/1986 | Kondo et al. | |
| 4,628,004 A | 12/1986 | Nickola et al. | |
| 4,629,464 A | 12/1986 | Takata et al. | |
| 4,654,314 A | 3/1987 | Takagi et al. | |
| 4,693,986 A | 9/1987 | Vit et al. | |
| 4,722,870 A | 2/1988 | White | |
| 4,772,287 A * | 9/1988 | Ray et al. | 623/17.12 |
| 4,794,046 A | 12/1988 | Nagai | |
| 4,810,685 A | 3/1989 | Twigg et al. | |
| 4,878,914 A | 11/1989 | Miwa et al. | |
| 4,950,294 A | 8/1990 | Hakamatsuka | |
| 4,957,509 A | 9/1990 | Tamari et al. | |
| 4,957,554 A | 9/1990 | Mathers et al. | |
| 4,960,426 A | 10/1990 | Atsumi | |
| 4,976,736 A | 12/1990 | White et al. | |
| 4,983,182 A | 1/1991 | Kijima et al. | |
| 5,001,169 A | 3/1991 | Nathan et al. | |
| 5,007,930 A | 4/1991 | Dorman et al. | |
| 5,030,396 A | 7/1991 | Saita et al. | |
| 5,037,438 A | 8/1991 | Davidson | |
| 5,061,660 A | 10/1991 | Park et al. | |
| 5,084,051 A | 1/1992 | Törmälä et al. | |
| 5,141,510 A | 8/1992 | Takagi et al. | |
| 5,152,791 A | 10/1992 | Hakamatsuka et al. | |
| 5,158,726 A | 10/1992 | Saita et al. | |
| 5,171,720 A | 12/1992 | Kawakami | |
| 5,185,177 A | 2/1993 | Kijima et al. | |
| 5,192,325 A | 3/1993 | Kijima et al. | |
| 5,205,921 A | 4/1993 | Shirkanzadeh | |
| 5,211,664 A | 5/1993 | Tepic et al. | |
| 5,231,169 A | 7/1993 | Constantz et al. | |
| 5,273,964 A | 12/1993 | Lemons | |
| 5,281,251 A | 1/1994 | Kenny et al. | |
| 5,282,861 A | 2/1994 | Kaplan | |
| 5,284,695 A | 2/1994 | Barlow et al. | |
| 5,296,180 A | 3/1994 | Hayes et al. | |
| 5,306,673 A | 4/1994 | Hermansson et al. | |
| 5,314,478 A | 5/1994 | Oka et al. | |
| 5,356,436 A | 10/1994 | Nonami et al. | |
| 5,366,508 A | 11/1994 | Brekke | |
| 5,397,362 A | 3/1995 | Noda | |
| 5,397,759 A | 3/1995 | Torobin | |
| 5,458,643 A | 10/1995 | Oka et al. | |
| 5,464,440 A | 11/1995 | Johansson | |
| 5,519,087 A | 5/1996 | Tang | |
| 5,520,861 A | 5/1996 | Powell et al. | |
| 5,522,894 A | 6/1996 | Draenert | |
| 5,531,794 A | 7/1996 | Takagi et al. | |
| 5,549,123 A | 8/1996 | Okuyama et al. | |
| 5,549,685 A | 8/1996 | Hayes | |
| 5,585,136 A * | 12/1996 | Barrow et al. | 427/2.24 |
| 5,624,674 A | 4/1997 | Seare, Jr. | |
| 5,626,861 A | 5/1997 | Laurencin et al. | |
| 5,629,186 A | 5/1997 | Yasukawa et al. | |
| 5,639,402 A | 6/1997 | Barlow et al. | |
| 5,645,593 A | 7/1997 | Woods et al. | |
| 5,676,699 A | 10/1997 | Gogolewski et al. | |
| 5,681,572 A | 10/1997 | Seare, Jr. | |
| 5,702,449 A | 12/1997 | McKay | |
| 5,714,103 A | 2/1998 | Bauer et al. | |
| 5,716,414 A | 2/1998 | Caldarise | |
| 5,725,813 A | 3/1998 | Nies | |
| 5,769,897 A | 6/1998 | Härle | |
| 5,776,193 A | 7/1998 | Kwan et al. | |
| 5,783,248 A | 7/1998 | Lin et al. | |
| 5,830,493 A | 11/1998 | Yokota et al. | |
| 5,876,446 A | 3/1999 | Agrawal et al. | |
| 5,876,449 A * | 3/1999 | Starck et al. | 623/23.7 |
| 5,899,939 A | 5/1999 | Boyce et al. | |
| 5,925,444 A | 7/1999 | Katsumura et al. | |
| 5,972,368 A | 10/1999 | McKay | |
| 5,976,454 A | 11/1999 | Sterzel et al. | |
| 6,010,336 A | 1/2000 | Shimotoso et al. | |
| 6,037,519 A | 3/2000 | McKay | |
| 6,039,762 A | 3/2000 | McKay | |
| 6,123,731 A | 9/2000 | Boyce et al. | |
| 6,210,612 B1 | 4/2001 | Pickrell et al. | |
| 6,214,049 B1 | 4/2001 | Gayer et al. | |
| 6,261,586 B1 | 7/2001 | McKay | |
| 6,302,913 B1 | 10/2001 | Ripamonti et al. | |
| 6,312,472 B1 | 11/2001 | Hall et al. | |
| 6,340,648 B1 | 1/2002 | Imura et al. | |
| 6,346,123 B1 | 2/2002 | McKay | |
| 2001/0018614 A1 | 8/2001 | Bianchi | |

FOREIGN PATENT DOCUMENTS

| | | | |
|---|---|---|---|
| EP | 0 585 978 A2 | 3/1994 | |
| EP | 0 714 666 A1 | 6/1996 | |
| JP | 4015062 A | 1/1992 | |
| WO | WO 9511752 A1 * | 5/1995 | |
| WO | WO 95/28973 A1 | 11/1995 | |
| WO | WO 99/16478 A1 | 4/1999 | |
| WO | WO 01/12106 A1 | 2/2001 | |

OTHER PUBLICATIONS

Camper, Yvonne, "Bone Grafts and Bone Substitutes", *Orthopedic Network News*, 1995, pp. 7-9, vol. 6, No. 4.

Chaki et al., "Strengthening Behavior of Hydroxyapatite-Silver Composite", *Ceramic Transactions*, 1995, pp. 235-244, vol. 48.

Constantz et al., "Skeletal Repair by Situ Formation of the Mineral Phase of Bone", *Science*, 1995, pp. 1796-1799, vol. 267.

Damien et al., "Bone Graft and Bone Graft Substitutes: A Review of Current Technology Applications ", *J. Applied Biometrics*, 1991, pp. 187-208, vol. 2.

Gao et al., "Enhanced Healing of Segmental Tibial Defects in Sheep by a Composite Bone Substitute Composed of Tricalcium Phosphate Cylinder, Bone Morphogenetic Protein, and Type IV Collagen", *J. Biomedical Materials Research*, 1996, pp. 505-512, vol. 32.

Ioku et al., "Dense/Porous Layered Apatite Ceramics Prepared by HIP Post-Sintering", *Journal of Materials Science Letters*, 1989, pp. 1203-1204, vol. 8, No. 10.

Ito et al., "Osteogenic Activity of Synthetic Hydroxylapatite with Controlled Texture—On the Relationship of Osteogenic Quantity with Sintering Temperature and Pore Size", *CRC Handbook of Bioactive Ceramics*, pp. 39-44, vol. 2.

Johnson et al., "Porous Ceramics as Bone Graft Substitutes in Long Bone Defects: A Biomechanical, Histological, and Radiographic Analysis", *J. Orthopedic Research*, 1996, pp. 351-369, vol. 14 No. 3.

Li et al., "High-Strength Biofunctional Zirconia: Mechanical Properties and Static Fatigue Behavior of Zirconia-Apatite Composites", *J. Materials Science: Materials in Medicine*, 1993, pp. 50-54.

Mattioli-Belmonte et al., "Osteoinduction in the Presence of Chitosan-Coated Porous Hydroxyapatite", *J. Bioactive and Compatible Polymers*, 1995, pp. 249-257, vol. 10.

McGee et al., "General Requirements for a Successful Orthopedic Implant", Chapter 13, *Encyclopedia of Biomaterials*, 1995, pp. 69-82.

Müller-Mai et al.,"Nanopatite and Organoapatite Implants in Bone: Histology and Ultrastructure of the Interface", *J. Biomedical Materials Research*, 1995, pp. 9-18, vol. 29.

Suda et al., "Biocompatibility of Zirconia Dispersed Hydroxyapatite Ceramics", *J. Jpn. Orthop. Assoc.*, 1990, pp. 75-84, vol. 64, No. 4.

Takaoka et al., "Ectopic Bone Induction on and in Porous Hydroxyapatite Combined with Collagen and Bone Morphogenetic Protein", *Clin. Orthop. Relat. Res.*, 1988, pp. 250-254, No. 234.

Tencer et al., "Mechanical and Bone Ingrowth Properties of a Polymer-Coated, Porous, Synthetic, Coralline Hydroxyapatite Bone Graft Material*a*", *Annals of New York Academy of Sciences*, 1988, pp. 157-172, vol. 23.

Tenhuisen et al., "Formation and Properties of a Synthetic Bone Composite: Hydroxyapatite-Collagen", *J Biomedical Materials Research*, 1995, pp. 803-810, vol. 29.

Tian et al., "A Novel Chondrocyte-Seeded Hydroxyapatite-Collagen Scaffold for Cartilage Repair", *Fifth World Biomaterials Congress*, May 29-Jun. 2, 1996.

Verheyen et al., "Hydroxylapatite/poly (L-lactide) Composites: An Animal Study on Push-Out Strengths and Interface Histology", *J. Biomedical materials Research*, 1993, pp. 433-444, vol. 27.

Wan et al., "Hydroxyapatite Modified Chitin as Potential Hard Tissue Substitute Material", *J. Biomedical Materials Research*, 1997, pp. 235-241, vol. 38, No. 3.

Wu et al., "Sintering of Hydroxylapatite-Zirconia Composite Materials", *J. of Materials Science*, 1988, pp. 3771-3777, vol. 23.

Zhang et al., "Porous Hydroxyapatite Reinforced with Collagen Protein", *Art. Cells, Blood Subs., and Immob. Biotech.*, 1996, pp. 693-702, vol. 24. No. 6.

\* cited by examiner

PROCESS FOR PRODUCING RIGID RETICULATED ARTICLES

STATEMENT OF RELATED APPLICATIONS

This application is a divisional of U.S. Ser. No. 09/440,144 (now U.S. Pat. No. 6,977,095), filed Nov. 15, 1999, which is incorporated by reference in its entirety. This application is a continuation-in-part, via 9/440,144, of U.S. Ser. No. 08/942,557 (now U.S. Pat. No. 6,136,029), filed on Oct. 1, 1997, which is incorporated by reference in its entirety. This application is related to U.S. Ser. No. 08/944,066 (now U.S. Pat. No. 6,296,667), filed on Oct. 1, 1997, which is also incorporated by reference in its entirety.

BACKGROUND OF THE INVENTION

1. Field of the Invention

The present invention relates in general to a process for producing bone substitute materials, and particularly to porous materials capable of supporting or encouraging bone ingrowth into its pores. The present invention also relates to a process for preparing a rigid reticulated article, such as a bone substitute material.

2. Description of Related Art

Bone substitute materials are described in copending application Ser. No. 08/942,557 (now U.S. Pat. No. 6,136,029) and Ser. No. 08/944,006 (now U.S. Pat. No. 6,296,667). A variety of materials have been proposed for use as bone substitute materials, ranging from shaped porous metal objects suitable for defect filling around knee and hip joint replacements on the one hand to shaped ceramic materials on the other. Ceramic materials by and large have been formed through a sintering process in which a powder of a ceramic material such as zirconia is compressed to a desired shape in a mold and is then heated to sintering temperatures. The porosity of the resulting material is commonly quite low. Materials employing calcium phosphates (for example: fluorapatite, hydroxyapatite, and tricalcium phosphate) can also be sintered in this manner, the calcium phosphate having the capacity for acting as a substrate for bone growth (osteoconductivity).

It has been suggested to mix ceramic powders such as zirconia and hydroxyapatite, and fluorapatite and spinel, and then compress the mixture in a mold and either sinter or hot isostatically press to produce a somewhat porous ceramic of zirconia having pores at least partially filled with hydroxyapatite. Reference is made to Tamari et al., U.S. Pat. No. 4,957,509, and also Aksaci, D. et al., Porous Fluorapatite/spinel Osteoceramic for Bone Bridges, Ceramic Transactions, Vol. 48 p. 283 (1995). It has also been suggested to use ceramic articles having both high porosity and low porosity portions, and reference is made here to Hakamatsuka et al., U.S. Pat. No. 5,152,791, Johansson, U.S. Pat. No. 5,464,440 and Borom, U.S. Pat. No. 4,237,559. See also Klawitter et al. U.S. Pat. No. 4,000,525. The latter reference refers to the use of an Al2O3 slip that is foamed into a sponge, followed by firing.

By and large, metal or ceramic materials that have been proposed for bone substitutes have been of low porosity. The art contains examples of substantially dense metals and ceramics with a semi-porous surface which is filled or coated with a calcium phosphate based material. The resulting structure has a dense metal or ceramic core and a surface which is a composite of the core material and a calcium phosphate, or a surface which is essentially a calcium phosphate. The bone substitute materials of this type commonly are heavy and dense, and often are significantly stiffer in structure than bone. Reference here is made to U.S. Pat. No. 5,306,673 (Hermansson et al.), U.S. Pat. No. 4,599,085 (Riess et al.), U.S. Pat. No. 4,626,392 (Kondo et al.), and U.S. Pat. No. 4,957,509 (Tamari et al.).

In addition to bone substitute materials described above, there are other applications in which the chemical, thermal, or other properties of a ceramic, metal, or other material can best be used in a porous form. One form of rigid porous materials with utility is the reticulated foam. A foam material is one with a large degree of volumetric porosity. This porosity is ideally fully open and fully interconnected. A common method of manufacture of these types of materials is to coat the surfaces of a polymeric foam with a slip of ceramic or metal, and then burn out the foam and other organics. The ceramic or metal coating is then sintered to leave a rigid foam with a structure largely similar to the starting polymeric foam. There are numerous examples of cellular, rigid foams in the known art and processes for producing these materials. See, for example, U.S. Pat. Nos. 4,000,525 and 5,061,660. However, the known art for producing rigid foam materials suffers from occluded openings and thus is not able to achieve a substantially fully open and interconnected porosity.

SUMMARY OF THE INVENTION

One object of the invention is to overcome the disadvantages of the known art described above. Another object of the invention is to provide a process for producing rigid, reticulated material, such as a bone substitute material, which is substantially open and interconnected, preferably fully open and interconnected, and can have smaller pore sizes than is possible with the known art. Yet another object of the invention is to provide a rigid, reticulated article.

In order to achieve the foregoing and further objects, there has been provided according to one aspect of the invention, a process for producing a rigid reticulated article, which includes the steps of:

(a) providing a first dispersion of a ceramic or metal powder, a binder, and a solvent;

(b) providing a reticulated substrate which has open, interconnected porosity;

(c) contacting the reticulated substrate with the first dispersion to coat the substrate with the dispersion to form a first coating;

(d) drying the coated reticulated substrate;

(e) contacting the reticulated substrate with one or more additional dispersions to form one or more additional coatings wherein the composition of the one or more additional coatings are the same or different from each other and the first coating;

(f) drying the additional coating between the steps of contacting;

(g) heating the coated reticulated substrate at a time and temperature sufficient to pyrolyze any organic components; and (h) sintering to form a ceramic or metal or composite reticulated article.

In a preferred embodiment, a successive dispersion has a lower viscosity than a preceding dispersion, and preferably, each dispersion has a lower viscosity than the preceding dispersion. In still another preferred embodiment, the substrate is a compliant polymeric foam.

In yet another preferred embodiment, the rigid reticulated article is a bone substitute material, and the first coating includes zirconia, the final coating includes hydroxyapatite calcium phosphate ceramic, and one or more intermediate coatings includes a combination of zirconia and hydroxyapatite calcium phosphate ceramic.

According to another aspect of the invention, there has been provided a process for producing a rigid reticulated article, which includes the steps of:

(a) providing a first dispersion of a metal or ceramic powder, a binder which becomes solvent-insoluble and flexible upon drying, and a solvent;

(b) providing a reticulated substrate which has open, interconnected porosity;

(c) contacting the reticulated substrate with the first dispersion to coat the substrate with the dispersion;

(d) drying the coated reticulated substrate;

(e) optionally contacting the reticulated substrate with one or more additional dispersions to form one or more additional coatings wherein the one or more additional coatings are the same or different from each other and the first coating;

(f) drying the additional coating between the steps of contacting;

(g) heating the coated reticulated substrate at a time and temperature sufficient to pyrolyze any organic components; and (h) sintering to form a ceramic or metal or composite reticulated article.

In a preferred embodiment, the binder is a polyacrylate emulsion which polymerizes upon drying.

According to yet another aspect of the invention, there has been provided a method of forming a ceramic article useful as a bone substitute and having an outer surface defining a shape having a bulk volume and having open, interconnecting openings extending throughout the volume and opening through the surface. The method includes providing an organic open-pore structure, coating the surfaces of pores of the structure with a ceramic slip, pyrolyzing the organic structure to leave a ceramic structure having struts defining a plurality of interconnecting interstices, and providing within the interstices a porous osteoconductive composition exposed to the interconnecting openings.

According to still another aspect of the invention, there has been provided a method of forming a ceramic article useful as a bone substitute and having an outer surface defining a shape having a bulk volume and having open, interconnecting openings extending throughout the volume and opening through the surface. The method includes providing an organic open-pore structure, coating the surfaces of pores of the structure with a ceramic slip comprising a strong, supportive ceramic material and a separate osteoconductive material, pyrolyzing the organic structure to leave a ceramic structure having struts defining a plurality of interconnecting interstices, and sintering the ceramic structure, said osteoconductive material being exposed to said interconnecting openings.

According to yet another aspect of the invention, there has been provided a rigid, reticulated article, which includes a first sintered ceramic or metal or composite material having an outer surface defining a shape having a bulk volume, interconnecting openings extending throughout said volume and opening through said surface, and struts bounding said interconnecting openings, wherein said material has at least 20 openings per inch.

Further objects, features and advantages of the present invention, will become readily apparent from detailed consideration of the preferred embodiments which follow.

DETAILED DESCRIPTION OF PREFERRED EMBODIMENTS

One aspect of the invention provides a process which can result in a strong, open-celled article that is useful as a bone substitute material and that is highly porous so as to accommodate bone ingrowth, is of low density, and which includes a material that fosters bone ingrowth.

In one embodiment, the process provides an open-celled article or reticulum having an outer surface defining a bulk volume and having interconnecting openings extending throughout the volume and opening through the outer surface. The article comprises a continuous strong supportive framework, preferably ceramic, having struts defining a plurality of interconnecting interstices throughout the bulk volume, and a porous osteoconductive composition carried by said supporting framework and exposed to the interconnected openings. The porous osteoconductive composition occupies at least a portion of the same bulk volume as the framework component. Desirably, the process produces articles having void volumes that are in the range of 20% to 90% and preferably at least 50%. Further, the mean size of the openings of the supportive framework component desirably are at least 50 µm and preferably are in the range of 200 µm to 600 µm.

In a preferred embodiment, the process of the invention provides a supportive framework and the osteoconductive composition which are each continuous three dimensional structures that exhibit 3-3 connectivity and occupy at least a portion and preferably the entirety of the same bulk volume, each continuous structure having interconnected openings that interconnect with the openings of the other. The osteoconductive composition may be carried within the openings of the supportive framework preferably as a continuous phase on the surface of the struts, and pores of the osteoconductive composition communicate with but may or may not be coextensive with the interstices of the supportive framework.

In yet another embodiment, the process provides struts which are comprised of a mixture or composite which contains the supportive material as well as osteoconductive material, the supportive material providing strength to the article and the osteoconductive material being carried at least partially on the surface of the interstices so as to be exposed to the interconnected openings to provide an osteoconductive environment favoring bone growth.

In one aspect of the invention, it is preferred to begin with the formation of a hard, strong, open framework having interstices in the size range of about 50 µm to about 1000 µm and preferably from about 200 µm to about 600 µm and having void volumes of at least about 30%, preferably at least about 50% and most preferably at least about 70%. The material of the framework may comprise any strong, hard, biologically-compatible material such as ceramic materials, metals and composites such as zirconia/hydroxyapatite or zirconia toughened alumina. Preferably, the framework component is of a ceramic material, zirconia and alumina being preferred.

In one preferred method, a slip of ceramic material is made by combining a ceramic powder such as zirconia with an organic binder and water to form a dispersion. The strut surfaces of an organic reticulated foam such as one of the various commercially available foams made of polyurethane, polyester, polyether, or the like are wetted and coated with the ceramic slip. The reticulated material may be immersed in the slip, and then removed and drained to remove excess slip. If desired, further excess slip can be removed by any of a variety of methods including passing the material between a pair of closely spaced rollers or by impacting the material with a jet of air. Varying the slip concentration, viscosity, and surface tension provides control over the amount of slip that is retained on the foam strut surfaces. Wetting agents and viscosity control agents also may be used for this purpose. A wide variety of reticulated, open cell materials can be employed, including natural and synthetic sponge materials and woven and non-woven materials, it being necessary in this embodiment only that the open cell material enables ceramic slip material to penetrate substantially fully through the openings in the structure.

Once the reticular struts are coated with slip, the slip solvent is removed by drying, accompanied desirably by mild heating, and the structure is then raised to sintering temperatures at which the ceramic particles at least partially sinter to one another to form a rigid, light framework structure that mimics the configuration of the reticular struts. Before reaching sintering temperatures, the slip-treated sponge desirably is held at a temperature at which the organic material pyrolyzes or burns away, leaving behind an incompletely sintered ceramic framework structure which then is raised to the appropriate sintering temperature.

Pyrolyzing or oxidizing temperatures for most organics are in the range of about 200° C. to about 600° C. Sintering temperatures for most ceramics of relevance to this invention are in the range of about 1100° C. to about 1600° C., and preferred sintering temperatures for metals are in the range of about 800 to about 1400° C. Zirconia and alumina or composites based on zirconia and alumina are the preferred ceramic materials for the structural elements. Examples of ceramic materials for the osteoconductive portion include calcium phosphates (e.g., hydroxyapatite, fluorapatite, and tricalcium phosphate and mixtures thereof), bioactive glasses, osteoconductive cements, and compositions containing calcium sulfate or calcium carbonate.

Metals which can be used to form the hard, strong, continuous framework component include titanium, stainless steels, cobalt/chrome alloys, tantalum, titanium-nickel alloys such as Nitinol and other superelastic metal alloys. Reference is made to Itin, et al., "Mechanical Properties and Shape Memory of Porous Nitinol," Materials Characterization [32] pp. 179-187 (1994); Bobyn, et al., "Bone Ingrowth Kinetics and Interface Mechanics of a Porous Tantalum Implant Material," Transactions of the 43rd Annual Meeting, Orthopaedic Research Society, p. 758, Feb. 9-13, 1997 San Francisco, Calif.; and to Pederson, et al., "Finite Element Characterization of a Porous Tantalum Material for Treatment of Avascular Necrosis," Transactions of the 43rd Annual Meeting, Orthopaedic Research Society, p. 598 Feb. 9-13, 1997. San Francisco, Calif., the teachings of all of which are incorporated by reference.

Metals can be formed into a hard, strong, continuous supportive frameworks by a variety of manufacturing procedures including combustion synthesis, plating onto a "foam" substrate, chemical vapor deposition (see U.S. Pat. No. 5,282,861), lost mold techniques (see U.S. Pat. No. 3,616,841), foaming molten metal (see U.S. Pat. Nos. 5,281,251, 3,816, 952 and 3,790,365) and replication of reticulated polymeric foams with a slurry of metal powder as described for ceramic powders.

The osteoconductive and osteoinductive materials that are appropriate for use in the present invention are biologically acceptable and include such osteoconductive materials as collagen and the various forms of calcium phosphates including hydroxyapatite; tricalcium phosphate; and fluorapatite, and such osteoinductive substances as: bone morphogenetic proteins (e.g., rhBMP-2); demineralized bone matrix; transforming growth factors (e.g., TGF-β); osteoblast cells, and various other organic species known to induce bone formation. Osteoinductive materials such as BMP may be applied to articles of the invention, for example, by immersing the article in an aqueous solution of this material in a dilute suspension of type I collagen. Osteoinductive materials such as TGF-β may be applied to an article of the invention from a saline solution containing an effective concentration of TGF-β.

The continuous supportive framework having interconnecting interstices or openings may be considered to be the primary load bearing element, and the osteoconductive material commonly is much weaker than the supporting framework. The supportive framework is preferably formed, as mentioned above, of a ceramic material such as zirconia. The framework structure is formed such that the interstices or openings themselves, on average, are wider than are the thicknesses of the struts which separate neighboring interstices. The load bearing framework is essentially completely continuous and self interconnected in three dimensions, and the void portion is also essentially completely continuous and self interconnected in three dimensions. These two three dimensionally interconnected parts are intercolated with one another. This can be referred to as a 3-3 connectivity structure where the first number refers to the number of dimensions in which the load bearing framework is connected, and the second number refers to the number of dimensions in which the void portion is connected. The concept of connectivity is explained at greater length in Newnham et al. "Connectivity and Piezoelectric-Pyroelectric Composites," Materials Research Bulletin, Vol. 13 pp. 525-536 (1978), the teachings of which are incorporated herein by reference. With the supporting framework described herein, the framework itself is given a 3 as it is connected in 3 dimensions, and the void portion is treated likewise. In contrast, partially sintered assemblages of powders invariably contain isolated pores or voids which are not connected to all other voids. A material with all isolated (that is, dead end) pores in a dense matrix would have 3-0 connectivity. A material having pores that pass completely through the matrix in one dimension would yield 3-1 connectivity, and a material having pores that interconnect two perpendicular faces but not the third would have 3-2 connectivity.

The opening sizes in the supportive framework preferably are at least about 50 μm and preferably are on the order of 200 μm to about 600 μm. It is preferred that there be substantially no pores or voids less than 50 μm. It should be understood that the openings in the supportive framework are of myriad irregular shapes. The interconnected openings or interstices through which biological ingrowth processes can take place define in three dimensions a labyrinth in which bone ingrowth and vascularization can occur; that is, the openings have many junctures with other openings to thus define tortuous pathways through the framework. In general, it is believed that in order to adequately support the growth of bone into the framework openings, the openings must be capable of accommodating the passage of tissue having transverse dimensions of at least about 50 µm. Conceptually, it is convenient to think of a 50 µm opening in materials of the invention as being capable of accommodating the passage through it of a "worm" having a round cross section and a transverse diameter of 50 µm. Put another way, a 50 µm opening should enable passage through it of a sphere having a 50 µm diameter. Although there is no completely satisfactory way known to us for measuring the opening sizes, it is possible to examine a scanning electron micrograph of a cross section of an article of the invention and viewing it as a planar projection of the structure, drawing several lines across the micrograph, measuring the openings that are intersected by the lines, and using averaging and standard deviation techniques to permit the size of the openings to be assessed.

An important feature of articles of the invention is that the interstices of the article remain at least partially open even with the presence of the osteoconductive and/or osteoinductive material. "Open", in this sense, means that the interstices are not plugged and that a fluid may pass entirely through the article from one side to the other.

Zirconia and other ceramics, when used to form the supportive framework, are exceedingly hard and are far more rigid than is bone. Although it would be desirable to employ as the supportive framework a material having a modulus of elasticity nearer to that of bone, bone substitute materials of the invention employing rigid materials having quite open interstices work well. It is believed that the ultimate union of bone with such porous articles during the healing process occurs over a large surface area and depth as the encroaching bone penetrates deeply into the interstices of the article. The substantial bone/ceramic interface that results enables forces to be readily transmitted to and from the ceramic framework with significantly less stress concentration in comparison to structures resulting from a bone/ceramic union that occurs within a small area of surface-to-surface contact and with little or no penetration of bone into the article.

When the osteoconductive material utilized is a ceramic, e.g., a calcium phosphate such as hydroxyapatite, for example, and the supportive framework is a ceramic such as zirconia, several methods according to this aspect of the invention may be employed in the manufacture of the article of the invention. The supportive zirconia framework structure can be fabricated as indicated above, by coating a slip of zirconia on the surface of the struts of a reticulated organic material such as a foam of polyurethane, polyester, polyether or the like, and subsequently raising the temperature of the coated foam to drive off slip solvent, to pyrolyze or burn off the organic foam material, and finally to heat the ceramic to cause the ceramic particles to at least partially sinter.

Once the ceramic framework has cooled, its struts may be coated with a slip containing a calcium phosphate (e.g., hydroxyapatite), the latter material forming a coating upon the framework material with excess slip draining from the framework structure. As pure calcium phosphate does not bond well to pure zirconia, it may be desirable to provide intervening layers which contain a fraction of both materials. The resulting material may again be heated to drive off the slip solvent and, if desired, to sinter the hydroxyapatite material to cause particles thereof to at least partially fuse to one another. In this configuration the resulting interstices of the supportive framework are open from one surface to the other, and the interstices of the second osteoconductive material are continuous, interconnect with one another, and interconnect with (and are coextensive with) the interstices of the supportive framework component.

In forming the article according to this aspect of the invention, it may be desirable to heat the zirconia framework component to a temperature at which the slip solvent has substantially all been driven off and partial sintering has begun, this condition being referred to as a partially sintered stage. At this point, a hydroxyapatite slip or composite zirconia and hydroxyapatite slip may be applied, the slip solvent driven off with heat, and the zirconia and hydroxyapatite are raised to a sintering temperature and sintered together.

In a modification of this embodiment described above, the slip of hydroxyapatite may have added to it viscosity control agents and a foaming agent such as hydrogen peroxide, or compressed gas. Upon introduction into the supportive zirconia framework structure of the hydroxyapatite slip, heating causes the slip to bubble and foam such that a number of smaller pores are formed in the hydroxyapatite matrix with the pores of the hydroxyapatite material nonetheless remaining substantially interconnected, continuous, and interconnecting with pores of the zirconia framework.

In another embodiment, the slip used to coat the polymeric foam and produce the reticulum contains fractions of both the supportive framework material (such as zirconia) and the osteoconductive material (such as hydroxyapatite). The reticulated polymeric substrate is coated with slip and the excess is allowed to drain. Further excess slip is removed by passing the article through squeeze rollers or by impacting the article with compressed air. The resulting material is heated to drive off solvent, to pyrolyze the organic constituents, and to co-sinter the two components of the composite. In the zirconia-hydroxyapatite system, the osteoconductive material is preferably included in a range of up to about 50 volume percent and more preferably about 10 to 25 volume percent with respect to the total zirconia/hydroxyapatite volume, sufficient osteoconductive material being used so as to provide an osteoconductive surface with respect to growing bone. Appropriate structures may use, for example, 25 volume percent of hydroxyapatite and 75% of YSZ (yttria-stabilized zirconia). The reticulated article that results has struts which are comprised of an intimate mixture of the two materials. The hydroxyapatite may appear as very small islands on the surface of the zirconia strut. In any event, in this embodiment, the osteoconductive material remains exposed to the openings in the article so as to provide an osteoconductive affect with respect to encroaching bone.

When the framework component is of metal, the two-part system with interconnected pores can be formed in the same manner as when the framework component is of ceramic materials, that is, the osteoconductive material may be incorporated within the struts or may be coated upon the walls of the metal struts, or foamed within the interstices and sintered. The processes described below in connection with the other aspects of the invention may also be used to form the bone substitute materials.

The bone substitute materials of the invention can be formed into the appropriate configurations for use as a bone substitute by several methods. In one preferred method, an organic material with open interstices such as a reticulated polyurethane foam is simply cut using ordinary cutting instruments such as scissors, scalpels, hot wire cutters and the like until it has the configuration desired. The thus configured foam material is used in any of the foregoing methods to produce the article of the invention. In another method, an organic foam such as that referred to earlier is coated with a zirconia or other ceramic slip and is heated to drive off solvent and convert the ceramic to the "green" state, at which point it can be shaped into the desired configuration. In a further method, a bone substitute of the invention which has been fully sintered can be shaped by standard machining methods such as sawing and grinding, water jet or laser cutting, etc.

If the supporting framework of the article is of metal, it can be shaped through appropriate machining to the desired form before introducing an osteoconductive or osteoinductive material. It is contemplated that the pores of a metal material may be first filled with wax and the resulting structure frozen so that the wax supports the metal structure during machining, following which the wax is simply melted to enable the wax to escape. This procedure may have utility particularly when the metal framework component comprises a very thin walled structure with large void openings, the struts of which, accordingly, can be unintentionally easily bent.

The articles produced by the present invention can then be further used with other materials, such as denser structural elements to form bone prosthesis as described in Ser. No. 08/942,577 (now U.S. Pat. No. 6,136,029).

In a further embodiment, articles of the invention comprise a supporting framework with added resilient materials, the framework itself having relatively large openings and a high void volume and being attached, as by sintering to a second, denser structural element which may be of the same or different material but which has smaller openings and a smaller void volume. Preferably, this denser portion is substantially fully dense, that is, it has a void volume less than 10%. The denser portion may take the form a semitubular plate, a rod useful as a stem receivable in the intramedullary canal of a long bone for a total hip or knee replacement, or a plate useful as a tibial tray of a knee prosthesis, etc. The latter material may be formed as a rod or stem, as may be useful for femoral hip stem prostheses or tibial tray prostheses, or may be formed as a thin layer relative to the first portion so that the resulting structure mimics natural bone in that the second portion may resemble cortical bone—the hard, dense, outer layer of a bone—whereas the first portion may be somewhat more open and porous and hence more closely resembles cancellous bone.

Figure 4:
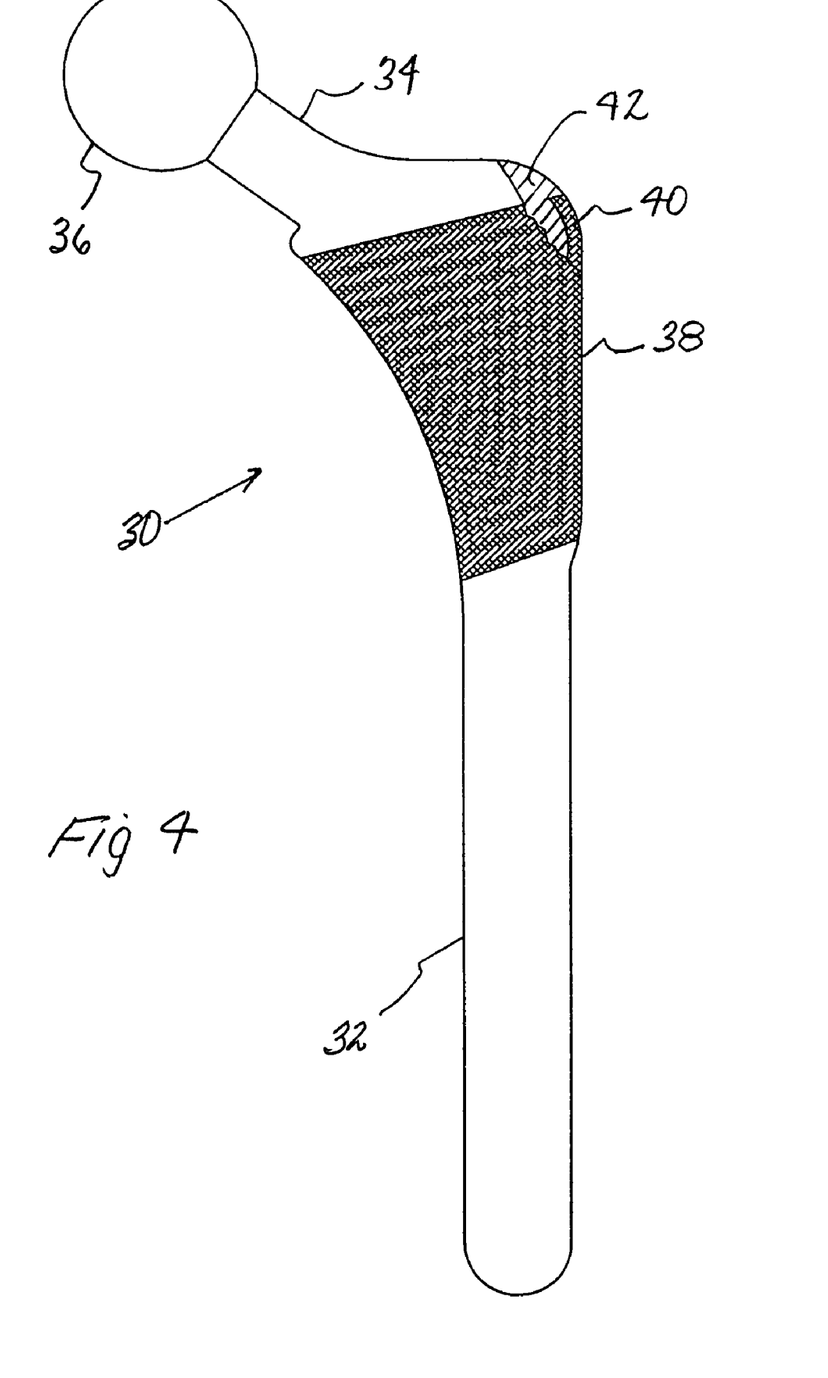
FIG. 4 is a broken away view of a femoral prosthesis utilizing an embodiment of the invention.

FIG. 4 shows a femoral hip stem prosthesis 30 made entirely of ceramic, the prosthesis having a dense stem portion 32, an angular neck 34 terminating in an articulating ball 36, and an angular shoulder portion 38. As shown in FIG. 4, the shoulder portion includes a thick layer 40 of an article of the invention having a framework with relatively large openings, carried by the denser portion 42 of the prosthesis. The coating 38 promotes bone ingrowth when the prosthesis has been implanted in the femur of a patent.

Figure 5:
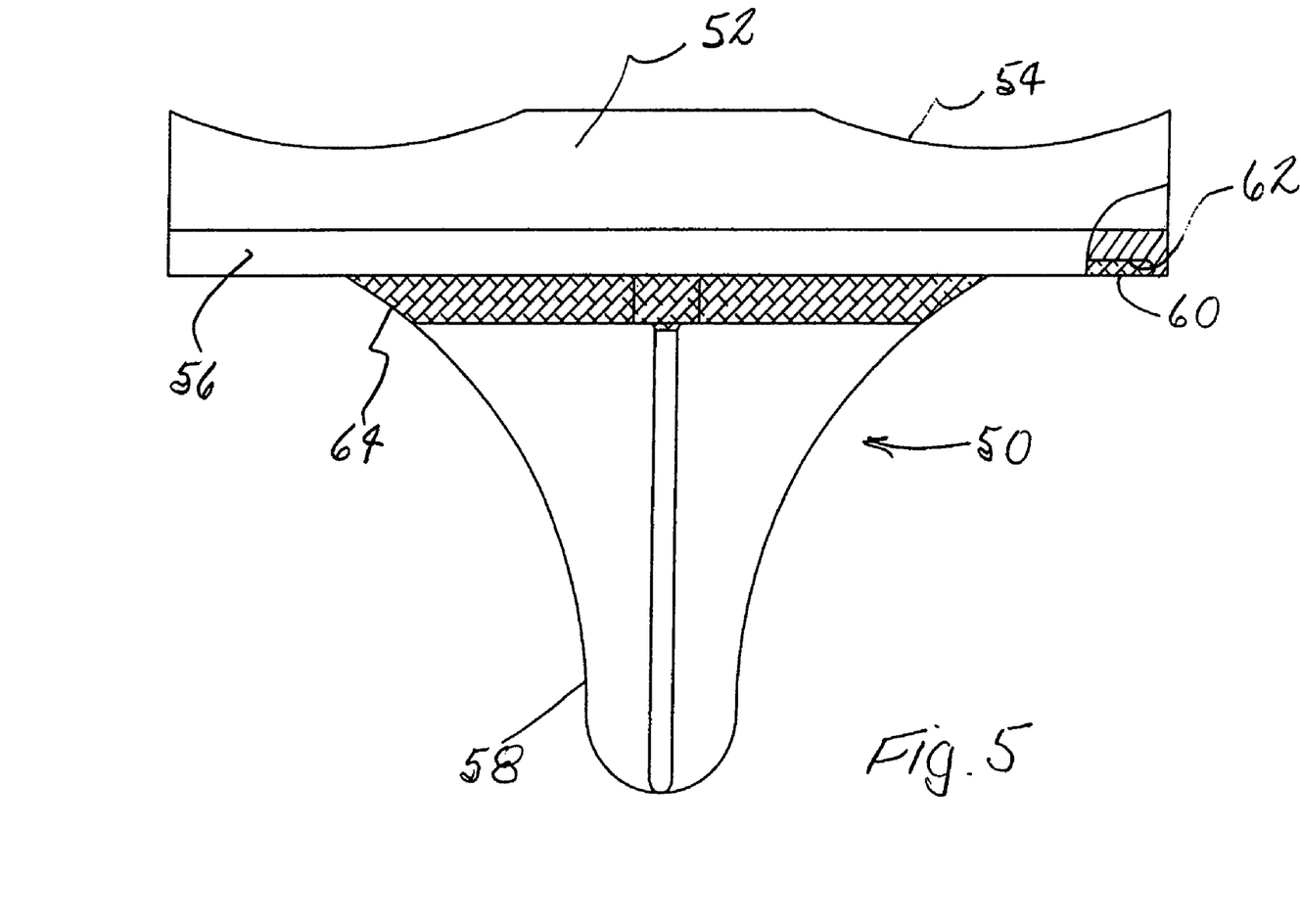
FIG. 5 is a broken away view of a tibial tray prosthesis utilizing an embodiment of the invention.

FIG. 5 depicts a tibial tray 50 having an upper plate 52 of ultra high molecular weight polyethylene having an articulating upper surface 54. The ultra high molecular weight polyethylene plate is supported by a plate 56 of the dense material of the invention, the plate 56 being integrally formed with a downwardly extending stem 58. The open framework material of the invention is shown in the form of a plate 60 which is received within a downwardly open recess 62 formed in the bottom of the plate 56, the framework 60 extending downwardly about the upper end of the stem, as shown at 64 in a relatively thick layer to promote bone ingrowth in this area.

The dense portion of the above described constructs can be prepared by any of the common ceramic forming techniques such as slip casting, tape casting, or coating and drying successive layers of slip onto a surface of a "foam" until a dense layer is formed. Dry pressing, injection molding and extrusion techniques may also be appropriate. The "green" dense portion is joined to the "green" low density portion through the use of a ceramic slip of substantially similar composition to the slip used in the formation of the low density portion or of a substantially similar composition to the slip used in the formation of the dense portion in the case of slip cast dense portion. "Green" here refers to the state of a ceramic article which has been formed and dried to a self-supporting structure but from which the organic constituents have not yet been removed. The dense portion may be alternatively comprised of a resorbable polymeric material, a resorbable ceramic material, or a resorbable composite material in addition to materials enumerated above.

During a surgical procedure, the openings of the articles of the invention may be filled with a calcium phosphate cement, to adhere the articles to bone, for example. The calcium phosphate cement hardens within the interstices and provides a secure bond to the articles.

This aspect of the invention may be more easily understood by reference to the following non-limiting examples:

EXAMPLE 1

A zirconia slip was prepared by combining the following ingredients and mixing them thoroughly by ball milling in a polyethylene container using zirconia media:

150 g partially stabilized zirconia powder (Zirconia Sales America)
2.25 g dispersant (Rohm and Haas, product D-3021)
15 g binder (Rohm and Haas product designation B-1000)
0.375 g surfactant/wetting agent (Air Products Surfynol™ TG)
0.26 g anti-foaming agent (Henkel Nopco™ NXZ)
36 ml deionized water.

Pieces of reticulated polyester-polyurethane foam 10-80 pores per inch (Stephenson and Lawyer) were immersed in the above slip and repeatedly compressed to remove air bubbles trapped inside. The foams were removed from the slip and the excess slip was allowed to drain. Further excess slip was removed by passing the foams between a pair of stainless steel squeeze rollers several times. The resulting pieces were allowed to dry at room temperature followed by drying at temperatures up to 100° C. in air. When the pieces appeared dry, they were heated to pyrolyze and remove organics (binder, dispersant, surfactant, anti-foam agent, and reticulated polymer foam) and then were sintered at a temperature of about 1400° C. for one hour. The preferred thermal cycle for the above involves raising the temperature of the pieces at the rate of 2° C. per minute to 600° C., holding the temperature at 600° C. for two hours, and then raising the temperature at the rate of 5° C. per minute to 1400° C., with a one hour hold at this temperature. The furnace is then cooled to room temperature at a rate of about 10° C. per minute.

The resulting product was a strong, light weight, porous zirconia framework or reticulum of zirconia having a void volume of about 76%. The framework was then coated with a slip containing both zirconia and hydroxyapatite. The slip was prepared by combining and ball milling, as described above, the following ingredients:

75 g partially stabilized zirconia (Zirconia Sales America)
12.89 g hydroxyapatite (Plasma Biotal)
1.5 g D-3021 dispersant
10 g B-1000 binder
0.25 g Surfynol™ TG surfactant/wetting agent
0.24 g Nopco NXZ anti-foaming agent
32 ml deionized water.

The hydroxyapatite provided 25% by volume of the combined hydroxyapatite and zirconia.

Figure 1:
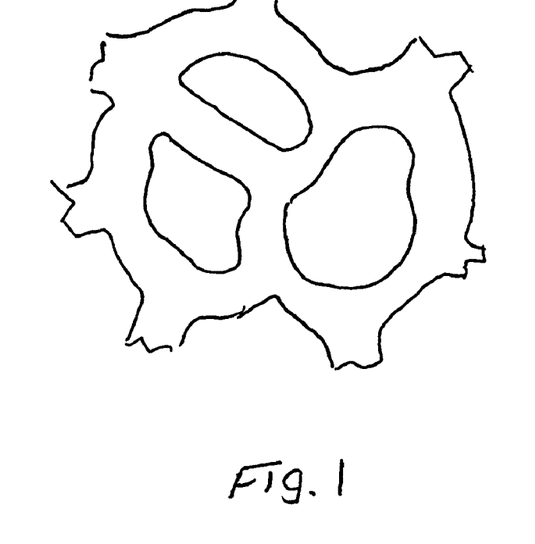
FIG. 1 is a schematic drawing of a ceramic based article of the invention illustrating the continuous open nature of the support structure.
Figure 2:
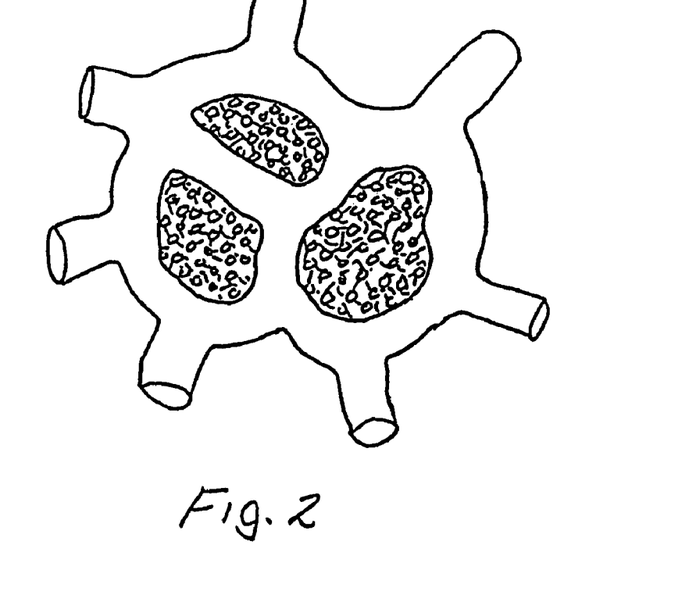
FIG. 2 is a schematic drawing of a ceramic based article of the invention illustrating an osteoconductive material foamed within the interstices of the supportive framework support.

Pieces of the zirconia prepared as described above were immersed in the slip and mechanically agitated to remove air bubbles and to assure complete penetration of the slip into the openings. Excess slip was allowed to drain, and further slip was removed with a stream of compressed air. The pieces were dried and were then raised at the rate of 5° C. per minute to a sintering temperature of 1400° C. and were held at this temperature for one hour. The resulting product comprises a strong ceramic framework of zirconia, the struts of which have a surface layer comprised of 75 volume percent zirconia and 25 volume percent hydroxyapatite. The structure of this product is illustrated in FIG. 1, and note may be made of the open nature of the zirconia supportive framework and the 3-3 connectivity of the framework and the hydroxyapatite.

If desired, an additional layer or layers may be added to the above structure. For example, in one embodiment, specimens of the above structure were immersed in a slip containing approximately 50% by volume of zirconia and hydroxyapatite, the specimens being drained, dried, and sintered as above at 1400° C.

EXAMPLE 2

This example describes the preparation of a zirconia-hydroxyapatite composite supporting framework, the struts of which bear a coating of hydroxyapatite.

Two ceramic slips were prepared. The first, comprising zirconia containing 15 volume percent hydroxyapatite and referred to as a ZHA-15 slip, was prepared by ball milling as in Example 1 using the following ingredients:

273.99 g partially stabilized zirconia
26.01 g hydroxyapatite (HiMed)
3 g poly(ethylene oxide) binder (Acros)
6 g dispersant (Darvan™ C, R. T. Vanderbilt)
0.75 g Surfynol™ TG surfactant/wetting agent
126 ml deionized water.

The second slip, referred to as an HA slip, was prepared by ball milling using the following ingredients:

50 g hydroxyapatite (HiMed)
0.5 g poly(ethylene oxide) binder (Acros)
0.125 g Surfynol™ TG surfactant/wetting agent
1 g dispersant (Darvan™ C, R. T. Vanderbilt)
76 ml deionized water.

Specimens of the reticulated polyester-polyurethane foam referred to in Example I were coated as in Example 1 with the ZHA-15 slip. The coated specimens were dried to the "green" state and then heat treated as in Example 1 to remove organic materials and were sintered at 1400° C.

Figure 3:
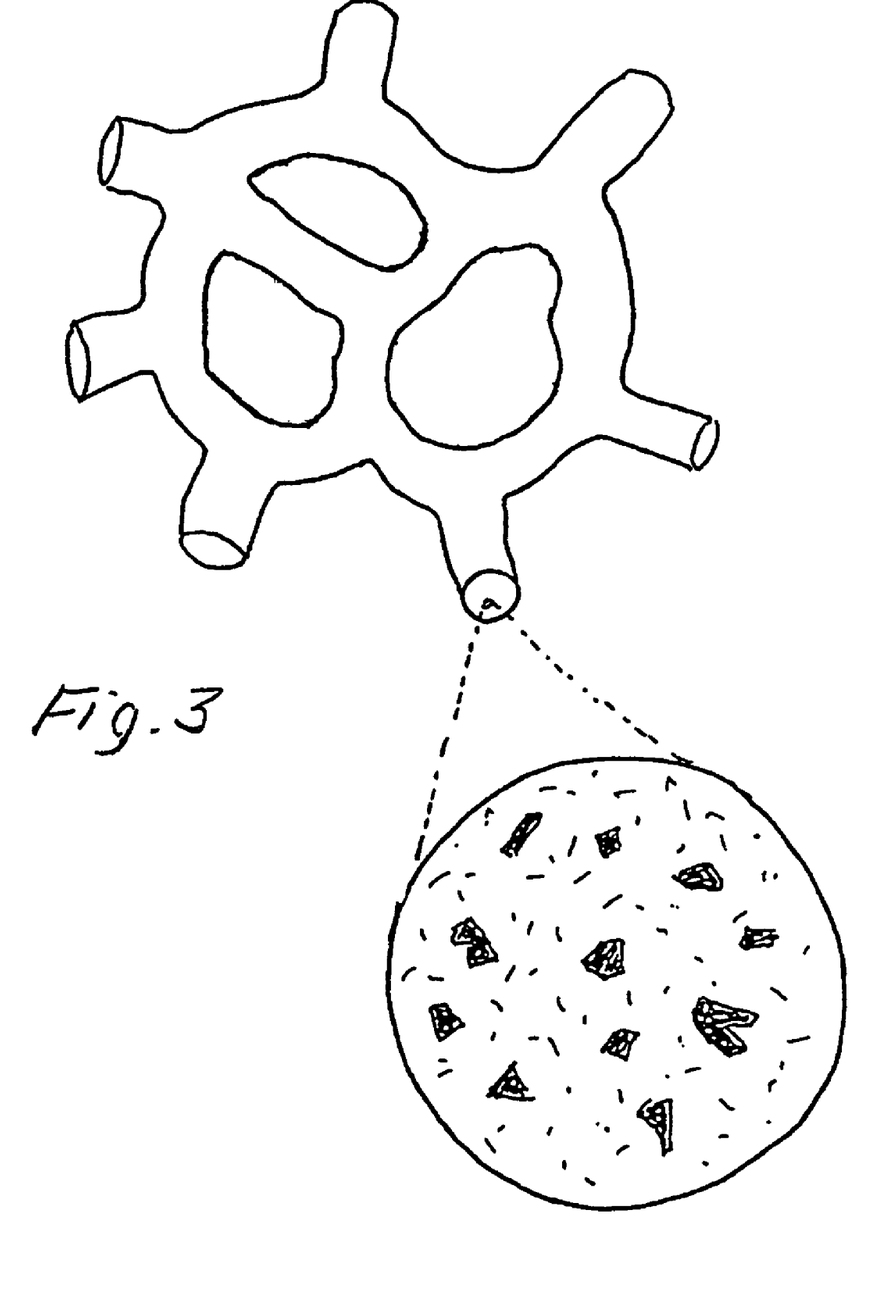
FIG. 3 is a drawing of an embodiment of the invention in which the struts are a composite containing both support and osteoconductive materials.

Depending upon the relative amounts of zirconia and hydroxyapatite that are used, the hydroxyapatite may appear as small "islands" on the surface of the struts; this is illustrated in FIG. 3. Sufficient hydroxyapatite or other osteoconductive material is employed so as to provide the surface of the struts with osteoconductive properties.

Following cooling, the specimens were coated with the HA slip, dried, heated to remove organic materials, and were sintered at 1400° C. The struts of the resulting structure were comprised of a core of partially stabilized zirconia composite with 15 volume percent hydroxyapatite and a surface layer of hydroxyapatite.

According to another aspect of the invention, the present inventors have found it possible to provide a rigid reticulated article which can have one or more of: a greater degree of openness and connectedness than is possible with known methods; very fine porosities greater than those possible with known methods; and multiple layers of the same or different material.

A dispersion is made by combining a metal powder or a ceramic powder with a binder and a solvent which is then contacted with a reticulated substrate to coat the substrate with the dispersion. The term "dispersion" is used synonymously with the term "slip" described above, in that both terms refer to a solvent which suspends a ceramic or metal powder, a binder and optional additives. After contacting the substrate with the dispersion, the substrate is removed and may be drained to allow removal of excess dispersion. Additional excess dispersion may be removed by rollers or by a jet of compressed air as described above. The coated substrate is then dried to remove at least a portion of the solvent. Drying may be accomplished by ways well known in the art.

In a preferred embodiment, the binder becomes solvent-insoluble and flexible upon drying. Preferably, the binder is employed as a relatively large volume fraction of the dispersion. The volume fraction can be at least 25 vol. %, more preferably at least 50 vol. % based on the entire volume of the solid components of the dispersion following drying. The use of such a binder, particularly at a relatively large volume fraction, provides an insoluble flexible film on the substrate that can be subsequently deformed without substantially cracking off, flaking off, or peeling off of the substrate. As used herein, "without substantially cracking off, flaking off, . . . " means that upon deformation, less than 10 wt %, preferably less than 5 wt %, based on the dried weight of the coating, and more preferably none of the coating is removed from the substrate. A preferred binder is a polyacrylate emulsion that polymerizes upon drying. While curing (i.e., polymerizing) by drying is preferred, any other means of curing such as the use of catalysts, radiation or gellation are also contemplated. Other preferred binders can include any polymer which becomes substantially insoluble in the carrier solvent upon drying.

In another preferred embodiment, additional coatings may be applied between the first drying and before sintering. Specifically, after the coated substrate is dried after the first contacting with the dispersion, the coated substrate is then contacted with a second dispersion which can be the same or a different composition. After contacting with the second dispersion, the excess second dispersion is then removed and the coated substrate is dried as described above. This can be repeated with additional coatings of dispersions. What then results is a substrate having greater than one, and preferably 2 to 6 coatings.

The use of multiple coatings is, in part, made possible by the use of dispersions having a lower viscosity than those used in the known art. Typical dispersions of the prior art generally have a viscosity which is on the order of 20,000 cP or higher. In contrast, the dispersions of the present invention, preferably have a viscosity which is 2500 cP or less. This allows substrates with very fine porosities to be coated multiple times while minimizing the clogging of the pores. The viscosities of successive dispersions may be generally the same or less than one or more of the preceding dispersions. In one embodiment, each successive dispersion has a lower viscosity than the preceding dispersions. Preferably, the viscosity of the first dispersion is from 200-2500 cP, the viscosity of the dispersion of the second coating is from 100-1500 cP, the viscosity of the dispersion of the third coating is from 50-800, and the viscosity of the dispersion of the fourth coating is 200 cP or less.

In a preferred aspect of multiple coatings, the flexible, solvent-insoluble binder described immediately above may also be used. The use of such a binder provides the solvent-insoluble, flexible film on the substrate that can be subsequently deformed without substantially cracking off, flaking off, or peeling off of the substrate as describe above. This is particularly useful when applying the subsequent coatings.

One advantage of multiple coatings is an article in which the original and final coatings are of a different composition, and there is one or more intermediate coatings which may be a composite of the original and final composition to form a functional gradient composite. A particularly useful article that results from this embodiment is one in which the core material (i.e., the first coating) is zirconia or alumina, and the surface material is an osteoconductive ceramic material such as a calcium phosphate material. This embodiment is useful for the substitution of natural bone.

Another useful embodiment of the invention is one in which the core material is zirconia, alumina, or another ceramic material, and the surface material is a catalyst material, in particular a ceramic catalyst material such as cerium oxide, or any of the perovskite ceramic catalysts such as lanthanum strontium cobalt iron oxide.

Another useful embodiment of the invention is one in which the reticulated material is prepared from a thermally stable material such as alumina or mullite, and the surface is made catalytically active with a catalytic coating such as platinum.

Fibers and/or whiskers may be added to the dispersion to provide a reinforced sintered article which has greater flexural, compressive and/or tensile strength. There is no limit as to the types of fibers or whiskers that may be used, other than the requirement that the fibers or whiskers be able to withstand the process conditions, including the sintering temperature. Suitable fibers or whiskers can include glass, metal, ceramics such as silicon nitride, silicon carbide, zirconia, alumina and carbon fibers, etc. The fibers or whiskers are generally added to the dispersion before the substrate is contacted with the dispersion. The fibers or whiskers may be added to only one or more than one of the dispersions. If the fibers or whiskers are added to multiple dispersions, they may be the same or different. A particularly preferred dispersion is one which contains hydroxyapatite. The length of the fibers or whiskers is solely dictated by their ability to be incorporated at least partially into the interior of the substrate, which in turn depends on the pore size of the substrate. A generally suitable range for most fibers or whiskers is in the micron or even submicron range, such as 0.1 to 100 microns.

The substrate is a reticulated substrate which can include the reticulated open cell materials described above. The reticulated substrate has open interconnected porosity (i.e., openings), preferably substantially fully open interconnected porosity, and more preferably fully open interconnected porosity. "Open interconnected porosity" is defined as the void portion being substantially continuous and self interconnected, preferably completely continuous and self-interconnected, preferably in three dimensions, and the material bounding the void portion is likewise substantially continuous and self interconnected, preferably, completely continuous and self interconnected, preferably in three dimensions. These two three-dimensionally interconnected parts are intercolated with one another and preferably have the "3-3 connectivity" as described above for the supporting framework. The pores of the substrate are open in that they are not plugged such that the dispersion may substantially pass entirely through the substrate and coat the available surfaces.

As noted above, one advantage of the present invention is that smaller porosity substrates may be used and the resulting reticulated article will still have the open interconnected porosity. The substrates may have at least 20, 50, 80, or 100 pores per inch or even greater, depending on the particular application. Suitable substrates can include polymeric foams, such as the polyester, polyurethane, polyether, and polyester-polyurethane foams described above and even natural sponges. Preferably, the substrate is "compliant" which is defined as deforming upon the application of an external force. The deformed substrate returns to at least a portion of, and preferably substantially all of its pre-deformation shape after the external force is removed. The substrate is preferably also wettable. Wettable in this instance is defined as being wettable by the solvent alone, or being rendered wettable by the use of known wetting agents.

The solvent can be any liquid capable of acting as a carrier for the inorganic powders and binder and can include water or organic solvents. In a preferred embodiment, water is employed as the solvent. Suitable organic solvents can include ethanol, methanol, toluene, methyl ethyl ketone, acetone, isopropyl alcohol, and xylene. The ceramic and metal powders may be the same as those described above and include the osteoconductive, osteoinductive and catalytic materials described above.

The dried, coated substrate is then pyrolyzed at a sufficient time and temperature to remove any organic components. The pyrolysis is generally conducted at temperatures described above. After pyrolysis, the remaining article is then heated at a time and temperature to sinter the article. The sintering is generally conducted at the temperatures described above. The configuration of the sintered article depends on its end use. For example, if the article is to be used as a bone substitute material, it will have the configuration of the bone or bone fragment it is replacing or another clinically relevant configuration. If the sintered article is to be used as a catalyst, it will have the appropriate catalytic configuration. The article may be configured at any stage, i.e., at the reticulated substrate stage, the "green" article stage (i.e., after drying), or the sintered article stage as described above with respect to the other aspects of the invention. The sintered article will preferably also have the substantially open, interconnected porosity or openings as described above for the substrates and can have a porosity identical to that of the substrate (i.e., at least 20, 50, 80, or 100 pores per inch).

After sintering, the rigid article may be subjected to further treatment depending on the end use. For example, if the article is to be used as a bone substitute material, the rigid article may be treated with osteoconductive materials such as collagen, and/or osteoinductive materials such as BMP, as described above, which cannot be subjected to sintering temperatures. These materials may be applied to the rigid article by methods known to those skilled in the art, such as by immersion, as also described above. The rigid article may also be further treated in a manner as described in copending application U.S. Ser. No. 08/944,006 (now U.S. Pat. No. 6,296,667).

This aspect of the invention may be more easily understood by reference to the following non-limiting examples:

EXAMPLE 3

A reticulated alumina foam with substantially open and interconnected porosity was prepared.

An alumina dispersion was prepared which contained the following:
10568 g Al2O3
1680 ml deionized H2O
3235 g B-1000
194 g D-3021
25 g Surfynol 420
50 g Nopco NXZ.

This dispersion was dispersed and mixed by ball milling in a polyethylene container with zirconia media. The viscosity of this dispersion was adjusted with deionized water. Pieces of reticulated polyester-polyurethane foam with 30-100 pores per inch (SIF—Stephenson and Lawyer) were cut. These foam pieces were immersed in the dispersion and compressed multiple times to remove air bubbles trapped inside. The foams were removed from the dispersion passed through rollers, and then the surface menisci were broken with a stream of compressed air. The "foams" were then allowed to dry at room temperature followed by drying at temperatures up to 100° C. in air. These coated foams were then subjected to a second coating process using the same dispersion adjusted to a lower viscosity in an identical manner to result in a "green" foam with a double coating of alumina dispersion. The double coated alumina foams were then coated again with a lower viscosity dispersion in a like manner. Following drying, these foams were coated a fourth time with a still lower viscosity dispersion and dried. Following complete drying, the foams were heated at 1 degree per minute to 600 degrees C. with a one hour soak to burn out the organic constituents. The foams were then further heated to 1550 degrees C. for one hour to sinter them and cooled at a rate of three degrees C. per minute to room temperature. The resulting alumina ceramic foams have substantially fully open and interconnecting porosity.

EXAMPLE 4

A reticulated structure with struts having a core of partially stabilized zirconia, an intermediate layer of zirconia 25 volume % hydroxyapatite composite (ZHA-25), and a surface layer of hydroxyapatite calcium phosphate ceramic was prepared. First, ceramic dispersions were prepared of zirconia, ZHA-25, and hydroxyapatite were prepared as follows.
  A zirconia dispersion was prepared which included:
    1000 g partially stabilized zirconia powder (Zirconia Sales America)
    15.31 g D-3021 dispersant (Rohm and Haas-Duramax)
    201.44 g B-1000 binder (Rohm and Haas-Duramax)
    5.01 g Surfynol 420 surfactant/wetting agent (Air Products)
    20.01 g Nopco NXZ anti-foaming agent (Henkel)
    210 ml deionized water.
  A ZHA-25 dispersion was prepared which included:
    229.1 g partially stabilized zirconia (Zirconia Sales America)
    39.58 g Hydroxylapatite (Plasma Biotal)
    4.3 g D-3021 dispersant (Rohm and Haas)
    61.45 g B-1000 binder (Rohm and Haas)
    1.26 g Surfynol 420 surfactant/wetting agent (Air Products)
    7.5 g Nopco NXZ anti-foaming agent (Henkel)
    75 ml deionized water.
  A hydroxyapatite dispersion was prepared which included:
    345.5 g Hydroxylapatite (Plasma Biotal)
    12.5 g D-3021 dispersant (Rohm and Haas)
    139.6 g B-1000 binder (Rohm and Haas)
    2.03 g Surfynol 420 surfactant/wetting agent (Air Products)
    10.02 g Nopco NXZ anti-foaming agent (Henkel)
    73.5 ml deionized water.
  These dispersions were dispersed and mixed by ball milling in a polyethylene containers with zirconia media. The zirconia dispersion was split into two equal volumes, and the viscosities of these two dispersions were adjusted to 700 and 365 cP respectively with deionized water. The viscosity of the ZHA-25 dispersion was adjusted to 160 cP, and the hydroxyapatite dispersion was adjusted to 85 cP with deionized water. Pieces of reticulated polyester-polyurethane foam with 30-80 pores per inch (SIF—Stephenson and Lawyer) were cut. These foam pieces were immersed in the 700 cP zirconia dispersion and compressed multiple times to remove air bubbles trapped inside. The foams were removed from the dispersion, passed through a pair of stainless steel rollers twice, and then the surface menisci were broken with a stream of compressed air. The "foams" were then allowed to dry at room temperature followed by drying at temperatures up to 100° C. in air. These coated foams were then subjected to a second coating process using the 365 cP zirconia dispersion in an identical manner to result in a "green" foam with a double coating of zirconia dispersion.
  The double coated zirconia foams were then coated with the ZHA-25 dispersion in a like manner. Following drying, these foams were coated with the hydroxyapatite dispersion and dried. Following complete drying, the foams were heated at 1 degree per minute to 600 degrees C. with a one hour soak to burn out the organic constituents. The foams were then further heated to 1400 degrees C. for one hour to sinter them and cooled at a rate of three degrees C. per minute to room temperature. The resulting foams have substantially fully open and interconnecting porosity. The struts which comprise the structure of these foams have a zirconia core and a hydroxyapatite surface. Between the core and surface is an intervening layer of zirconia-hydroxyapatite composite with 25 volume percent hydroxyapatite.

EXAMPLE 5

A reticulated structure was prepared where the struts had a core of partially stabilized zirconia, an intermediate layer of zirconia 40 volume %—hydroxyapatite composite, and a surface layer of hydroxyapatite calcium phosphate ceramic. First, ceramic dispersions were prepared of zirconia, zirconia-hydroxyapatite composite with 40 volume percent HA (ZHA-40), and hydroxyapatite were prepared as follows.
  A zirconia dispersion was prepared which included:
    1000 g partially stabilized zirconia powder (Zirconia Sales America)
    15.31 g D-3021 dispersant (Rohm and Haas-Duramax)
    201.44 g B-1000 binder (Rohm and Haas-Duramax)
    5.01 g Surfynol 420 surfactant/wetting agent (Air Products)
    20.01 g Nopco NXZ anti-foaming agent (Henkel)
    210 ml deionized water.
  A ZHA-40 dispersion was prepared which included:
    184.11 g partially stabilized zirconia (Zirconia Sales America)
    63.62 g Hydroxylapatite (Plasma Biotal)
    5.20 g D-3021 dispersant (Rohm and Haas)
    61.80 g B-1000 binder (Rohm and Haas)
    1.26 g Surfynol 420 surfactant/wetting agent (Air Products)
    7.5 g Nopco NXZ anti-foaming agent (Henkel)
    80 ml deionized water.
  A hydroxyapatite dispersion was prepared which included:
    345.5 g Hydroxylapatite (Plasma Biotal)
    12.5 g D-3021 dispersant (Rohm and Haas)
    139.6 g B-1000 binder (Rohm and Haas)
    2.03 g Surfynol 420 surfactant/wetting agent (Air Products)
    10.02 g Nopco NXZ anti-foaming agent (Henkel)
    73.5 ml deionized water.
  These dispersions were dispersed and mixed by ball milling in a polyethylene container with zirconia media. The zirconia dispersion was split into two equal volumes, and the viscosities of these two dispersions were adjusted to 700 and 365 cP respectively with deionized water. The viscosity of the ZHA-40 dispersion was adjusted to 160 cP, and the hydroxyapatite dispersion was adjusted to 85 cP with deionized water. Pieces of reticulated polyester-polyurethane foam with 30-80 pores per inch (SIF—Stephenson and Lawyer) were cut. These foam pieces were immersed in the 700 cP zirconia dispersion and compressed multiple times to remove air bubbles trapped inside. The foams were removed from the dispersion, passed through a pair of stainless steel rollers twice, and then the surface menisci were broken with a stream of compressed air. The "foams" were then allowed to dry at room temperature followed by drying at temperatures up to 100° C. in air.

These coated foams were then subjected to a second coating process using the 365 cP zirconia dispersion in an identical manner to result in a "green" foam with a double coating of zirconia dispersion. The double coated zirconia foams were then coated with the ZHA-40 dispersion in a like manner.

Following drying, these foams were coated with the hydroxyapatite dispersion and dried. Following complete drying, the foams were heated at 1 degree per minute to 600 degrees C. with a one hour soak to burn out the organic constituents. The foams were then further heated to 1400 degrees C. for one hour to sinter them and cooled at a rate of three degrees C. per minute to room temperature. The resulting foams have substantially fully open and interconnecting porosity. The struts which comprise the structure of these foams have a zirconia core and a hydroxyapatite surface. Between the core and surface is an intervening layer of zirconia-hydroxyapatite composite with 40 volume percent hydroxyapatite.

EXAMPLE 6

A stainless steel reticulated foam was prepared.
First, a dispersion was prepared which included:
715 g 316 Stainless steel powder (Anval)
7.5 g D-3021 dispersant (Rohm and Haas)
100.5 g B-1000 binder (Rohm and Haas)
2.5 g Surfynol 420 surfactant/wetting agent (Air Products)
10 g Nopco NXZ anti-foaming agent (Henkel)
105 ml deionized water.

This dispersion was dispersed and mixed by ball milling in a polyethylene container with zirconia media. Pieces of reticulated polyester-polyurethane foam with 60 pores per inch (SIF—Stephenson and Lawyer) were cut. These foam pieces were immersed in the dispersion and compressed multiple times to remove air bubbles trapped inside. The foams were removed from the slip, passed through rollers, and then the surface menisci were broken with a stream of compressed air. The "foams" were then allowed to dry at room temperature followed by drying at temperatures up to 100° C. in air.

Following complete drying, the foams were heated at 1 degree per minute to 600 degrees C. with a one hour soak to burn out the organic constituents. The foams were then further heated to 1200 degrees C. for one hour in a hydrogen atmosphere to sinter them and cooled at a rate of three degrees C. per minute to room temperature. The resulting stainless steel foams have substantially fully open and interconnecting porosity.

While a number of preferred embodiments of the present invention have been described, it should be understood that various changes, adaptations and modifications may be made therein without departing from the spirit of the invention and the scope of the appended claims.

What is claimed is:

1. A method of forming a ceramic article useful as a bone substitute and having an outer surface defining a shape having a bulk volume and having open, interconnecting openings extending throughout said volume and opening through said surface, the method comprising providing an organic open-pore structure, coating surfaces of pores of the structure with a ceramic slip comprising zirconia, a binder, a solvent, fibers and/or whiskers, and hydroxyapatite, wherein the hydroxyapatite is present in an amount of up to about 50 volume percent based on the total volume of zirconia and hydroxyapatite, pyrolyzing the organic structure to leave a ceramic structure having struts defining a plurality of interconnecting interstices, and sintering the ceramic structure, said osteoconductive material being exposed to said interconnecting openings.

2. A method of claim 1, including the step of shaping said organic open-pore structure to a predetermined configuration before coating the pores thereof with said ceramic slip.

3. A method of claim 1, including the step of shaping said organic open-pore structure to a predetermined configuration after coating the pores thereof with said ceramic slip.

4. A method of claim 1 including the step of inserting a calcium phosphate bone cement into said openings.

5. A method of claim 1, wherein the hydroxyapatite is present in an amount of about 10 to about 25 volume percent based on the total volume of the zirconia and the hydroxyapatite.

6. A method of claim 1, further comprising the step of sintering the ceramic structure to a second, denser structural element.

7. A method of claim 1, wherein the fibers and/or whiskers comprise a material selected from the group consisting of glass, metal, and ceramic.

8. A method of claim 7, wherein the ceramic is selected from the group consisting of silicon nitride, silicon carbide, zirconia, alumina, and carbon.

9. A method of claim 1, wherein the length of the fibers and/or whiskers is from about 0.1 to about 100 microns.

10. A method of claim 1, further comprising contacting the struts with a porous osteoconductive coating either before or after said sintering step.

11. A method of claim 10, wherein the porous osteoconductive composition comprises an osteoconductive material selected from the group consisting of collagen, calcium phosphates, bone morphogenetic proteins, demineralized bone matrix, transforming growth factors, and osteoblast cells.

12. A method of claim 10, wherein the porous osteoconductive coating comprises hydroxyapatite.

13. A method of claim 1, wherein the ceramic structure comprises interstices having a size range of about 50 µm to about 1000 µm and a void volume of at least about 30%.

14. A method of claim 1, wherein the zirconia is yttria-stabilized zirconia.

15. A method of producing a rigid reticulated article, comprising:
(a) providing a first dispersion of a metal or ceramic powder, a binder comprising a polyacrylate emulsion that polymerizes upon drying, and a solvent;
(b) providing a reticulated substrate which has open, interconnected porosity;
(c) contacting the reticulated substrate with the first dispersion to coat the substrate with the dispersion;
(d) drying the coated reticulated substrate;
(e) optionally contacting the reticulated substrate with one or more additional dispersions to form one or more additional coatings wherein the one or more additional coatings are the same or different from each other and the first coating;

(f) drying the additional coating between the steps of contacting;

(g) heating the coated reticulated substrate at a time and temperature sufficient to pyrolyze any organic components;

(h) sintering to form a ceramic or metal or composite reticulated article; and further comprising the step of adding fibers and/or whiskers to at least one of the first dispersion and the one or more additional dispersions.

16. A method of claim 15, wherein the fibers and/or whiskers comprise a material selected from the group consisting of glass, metal, and ceramic.

17. A method of claim 16, wherein the ceramic is selected from the group consisting of silicon nitride, silicon carbide, zirconia, alumina, and carbon.

18. A method of claim 15, wherein the fibers and/or whiskers are added to more than one of the first dispersion and the one or more additional dispersions, and wherein the fibers and/or whiskers may comprise the same or different material.

19. A method of claim 15, wherein the length of the fibers and/or whiskers is from about 0.1 to about 100 microns.

20. A method of claim 15, wherein the volume fraction of binder is at least about 25 vol. % based on the entire volume of the solid components of the dispersion following drying.

* * * * *